US00PP08553P

United States Patent [19]

Staton

[11] Patent Number: Plant 8,553

[45] Date of Patent: Jan. 18, 1994

[54] ZOYSIA GRASS PLANT 'Z-3'

[75] Inventor: Thomas A. Staton, Waimanalo, Hi.

[73] Assignee: Quality Turfgrass, Waimanalo, Hi.

[21] Appl. No.: 739,328

[22] Filed: Aug. 1, 1991

[51] Int. Cl.[5] ..... A01H 5/00
[52] U.S. Cl. ..... Plt./90
[58] Field of Search ..... Plt. 90

U.S. PATENT DOCUMENTS

| | | | |
|---|---|---|---|
| PP6345 | 10/1988 | Whiting | PLT.90 |
| PP6516 | 1/1989 | Whiting | PLT.90 |
| PP6529 | 1/1989 | Pursley | PLT.90 |
| PP7074 | 12/1989 | Whiting | PLT.90 |

*Primary Examiner*—James R. Feyrer
*Attorney, Agent, or Firm*—Keck, Machin & Cate

[57] ABSTRACT

I disclose that my herein invention of a new variety of Zoysia grass plant was discovered by me as a found seedling in a pot of sterile medium on my farm in Waimanalo, Oahu, Hawaii. This new discovered Zoysia grass plant is a perennial, which exhibits an attractive deep green color, color Green number 141 A, as defined by The Royal Horticultural Society of London Colour Chart, of a low decumbent dense growth habit, that produces outstanding vigorous growth and a prolific rhizome system. The anthers are dark purplish-red color, color Red-Purple 61 B; the stigmas are pale yellow-green, color Yellow-Green 150 D. The entire plant of the new claimed variety of Zoysia grass plant, is glabrous except for several short hairs at the top of the leaf sheath at the sides of the ligule.

2 Drawing Sheets

BACKGROUND AND SUMMARY OF THE INVENTION

The present invention relates to a new and distinct variety of Zoysia grass plant which was disovered by me, growing as a newly found seedling in a tray of sterile, inert, volcanic cinder on my farm in Waimanalo, Oahu, Hawaii. About fifty trays filled with undecomposed, insert, sterile volcanic cinder had been set in the field on plastic sheets between mature flowering stands of 'El Toro' Zoysia grass (*Zoysia japonica*) and Hawaiian 'Emerald' Zoysia grass (*Zoysia matrella* type). It should be noted that what is commonly referred to as 'Emerald' Zoysia grass in Hawaii is distinctly different from 'Emerald' Zoysia grass (*Zoysia japonica*×*Zoysia tenuifolia*) imported from U.S. Department of Agriculture, Beltsville, Md. and more closely resembles, but is not identical to, *Zoysia matrella* imported from Auburn University, Auburn, Ala.; therefore, I have categorized Hawaiian 'Emerald' Zoysia as a *Zoysia matrella* type. The cinder-filled trays, used to germinate various palm seeds, were observed by me to have a number of Zoysia grass seedlings growing in them. Since the trays were surrounded by mature, flowering stands of 'El Toro' Zoysia grass and Hawaiian 'Emerald' Zoysia grass, it was assumed that the origin of the seedlings was from the surrounding Zoysia grasses. Over a period of approximately 3 months, several hundred Zoysia grass seedlings were observed for desireable growth characteristics and removed from the cinder-filled trays. Most were immediately discarded because of undesireable characteristics such as poor vigor or color, but several dozen selections were retained and planted in sterile medium in trays. Following continued observation for desireable growth characteristics, all but 20 of the selections were discarded; the 20 remaining selections were increased by me by dividing sufficient stolon and rhizome material of each selection to further replant each of the 20 selections into ten 10" by 20" flats. Following observation for desireable characteristics, one selection, designated 'Z-3', showed superior and unique growth characteristics as follows: exceptional vigor, low decumbent growth habit, lusterous attractive leaf color, leaf blades softer to the touch than 'El Toro' Zoysia grass or Hawaiian 'Emerald' Zoysia grass, leaf size intermediate between 'El Toro' Zoysia grass and Hawaiian 'Emerald' Zoysia grass, and a very dense, tight growth habit without excessive formation of thatch. In 1988, the ten flats of 'Z-3' stolon and rhizome material were divided by me and planted out into the soil in an area of 15' by 30', and fertilized and mowed regularly to form a turfgrass surface, for observation of growth habit, flowering characterics, and phenotypic stability. In early summer 1992, stolons and rhizomes were extracted from this plot by me and planted both in a composted wood shavings/horse manure medium on plastic on beds totalling 5,000 ft2, and in the soil together with 'El Toro' Zoysia grass and Hawaiian 'Emerald' Zoysia grass in three adjacent 12' by 12' plots for comparative observation. All plantings were at our farm in Waimanalo, Oahu, Hawaii. Under identical growing conditions and planting rates, the following phenotypic differences were measured: Z-3 Zoysia grass: culms 5–6.5 centimeters; first mature leaf 2–3 millimeters in width, 5–7 centimeters long; stolons a dark purplish-red color, color Red-Purple, number 61 B of The Royal Horticultural Society of London Colour Chart, 1.5 millimeters in width with nodes 1.2–2 centimeters apart, versus 'El Toro' Zoysia grass: culms 10–15 centimeters; first mature leaf 3–4 millimeters in width, 15–20 centimeters long; stolons a dark purplish-red color, color Red-Purple, number 59 A of The Royal Horticultural Society of London Colour Chart, 2 millimeters in width with nodes 1.5–2 centimeters apart, versus Hawaiian 'Emerald' Zoysia grass: culms 3–5.5 centimeters; first mature leaf 1.3–1.7 millimeters in width, 4–6 centimeters long; stolons a dark purplish-red color, color Red-Purple number 59 B of The Royal Horticultural Society of London Color Chart. In addition, it was noted that, under identical growing conditions and planting rates, Z-3 Zoysia grass covered the ground in approximately 3 months, faster than Hawaiian 'Emerald' Zoysia grass, and slightly slower than 'El Toro' Zoysia grass; the resultant sod grew as densely as Hawaiian 'Emerald' Zoysia grass, and more densely than 'El Toro' Zoysia grass; the leaves were softer to the touch than either Hawaiian 'Emerald' Zoysia grass or 'El Toro' Zoysia grass; the root density of Z-3 Zoysia grass was greater than that of Hawaiian 'Emerald' Zoysia grass, and approximately equal to that of 'El Toro' Zoysia grass; Z-3 Zoysia grass had 189 rhizomes per square decimeter versus 112 rhizomes for 'El Toro' Zoysia grass and 171 rhizomes for Hawaiian 'Emerald' Zoysia grass; thatch formation of Z-3 Zoysia grass was much less than that of Hawaiian 'Emerald' Zoysia grass, and somewhat more than that of 'El Toro' Zoysia grass; seedheads of Z-3 Zoysia grass were much less conspicuous than those of either Hawaiian 'Emerald' Zoysia grass or 'El Toro' Zoysia grass; maximum height of unmowed Z-3 Zoysia grass was 15–20 centimeters, the same as Hawaiian 'Emerald' Zoysia grass and less than the 30–40 centimeter height of 'El Toro' Zoysia grass. Although the parentage of Z-3 Zoysia grass is uncertain, because of its many intermediate phenotypic characteristics and the position of the original found seedling between mature flowering stands of 'El Toro' Zoysia grass and Hawaiian 'Emeral' Zoysia grass, it may be assumed to be a hybrid between these two. Since it more closely resembles 'El Toro' Zoysia grass than Hawaiian 'Emerald' Zoysia grass, it could also be a self-pollinated offspring of 'El Toro' Zoysia grass, or it could have come from another, unknown source.

Flowers of Z-3 Zoysia grass have produced seeds, whose viability is as yet untested. A plot of unmowed Z-3 Zoysia grass survived and maintained its original color without any irrigation or fertilizer during a 6 month warm dry summer season period, suggesting its potential for low water and fertilizer imputs. In Manatee County, Fla., Z-3 Zoysia grass planted next to 'El Toro''Meyer', and 'Emerald' Zoysia grass showed no damage from hunting billbugs during the 1992 summer season, whereas the other Zoysia grasses showed severe to moderate damage; and Z-3 Zoysia grass submerged in flood water for 2 days showed no color loss, whereas 'Meyer' and 'Emerald' Zoysia grass showed color loss. Z-3 Zoysia grass is well-adapted to semi-tropical Hawaii, but its cold-hardiness is as yet untested. The novelty and potential advantages of Z-3 Zoysia grass when compared to the closest known varieties of Zoysia grasses, 'El Toro' Zoysia grass and Hawaiian-'Emerald' Zoysia grass are as follows: its very dense, tight, decumbent growth habit, with the resultant potential to block out emerging weeds; its proliferation of rhizomes, with the potential for superior recovery from damage or sod-harvesting; its very inconspicious seedheads, low growth habit, and minimal thatch accumulation, with the potential for less frequent mowing or use as an unmowed ground cover; its softer leaf blades, with the potential for more comfortable home lawn activities; and its deep green lusterous intermediate-textured leaves, with the potential for a more pleasing aesthetic appearance. Continued asexual propagation by me through stolons and rhizomes of this new variety of Zoysia grass plant, has confirmed that clones of the claimed plant have been found to retain all of the distinguishing characteristics of the originally discovered seedling, and the plant thereby has been established to be stable.

A primary object of the invention is to provide a new and distinct variety of Zoysia grass having the desireable characteristics referred to above and described in detail below:

BOTANICAL DESCRIPTION OF THE PLANT

Figure 1:
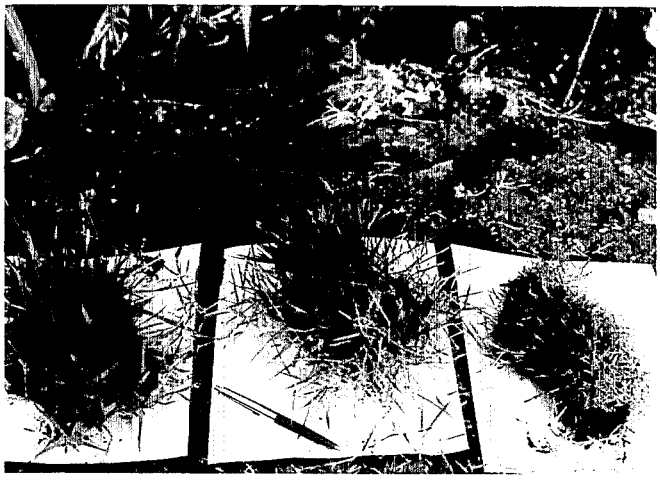
FIG. 1 is a photograph of an unmowed clump of the variety.

A detailed description of the new and distinct variety of Zoysia grass plant Z-3 is:

(a) An attractive deep lusterous green color, color Green number 141 A of The Royal Horticultural Society of London Colour Chart.
(b) The grass is low-growing, decumbent in habit.
(c) The grass spreads by stolons and rhizomes, forming a dense, uniform surface, with an extensive root system. The stolons are a dark purplish-red color, color Red-Purple, number 61 B of The Royal Horticultural Society of London Colour Chart; stolons 1.5 millimeters in width with nodes 1.2–2 centimeters apart.
(d) Culms vary in height from 5–6.5 centimeters.
(e) Leaves rolled in bud shoot.
(f) The leaf blade is glabrous, flat, and gradually tapering to an acute point.
(g) The first mature leaf is 2–3 millimeters in width and 5–7 centimeters long.
(h) The ligule is a very small ciliate fringe.
(g) Auricles are absent.
(h) The collar is broad, and continuous.
(i) The sheath is glabrous, except for several hairs less than 1 millimeter in length at the top of the sheath at the sides of the ligule; the sheath is split with separate margins.
(j) The entire plant is glaborous, except at the top of the sheath where several hairs are present at the sides of the ligule.
(k) The inflorescence consists of a single spike at the top of the main stem.
(l) The spike contains stigmas of pale yellow-green color, color Yellow-Green 150 D of The Royal Horticultural Society of London Colour Chart, and anthers of dark purplish-red color, color Red-Purple 61 B of The Royal Horticultural Society of London Colour Chart; the glumes are 2–3 millimeters long, blunt at their base, pointed at their tips.

I claim:

1. A new and distinct variety of grass plant, Zoysia Z-3 as herein described and illustrated.

* * * * *

UNITED STATES PATENT AND TRADEMARK OFFICE

CERTIFICATE OF CORRECTION

PATENT NO. : Plant 8,553
DATED : January 18, 1994
INVENTOR(S) : Thomas A. STATON

It is certified that error appears in the above-identified patent and that said Letters Patent is hereby corrected as shown below:

Title page,
under, Attorney, Agent or Firm, replace "Machin" with --Mahin--.

Col. 3, line 18, replace "Emeral" with --Emerald--.

Figure 2:
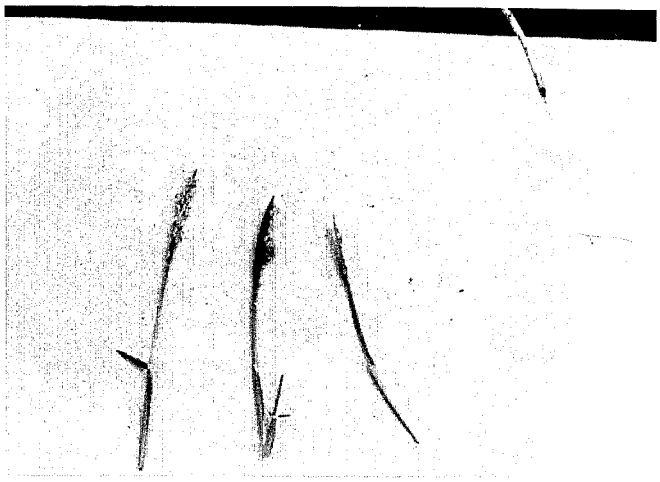
FIG. 2 is a photograph of a closely mowed clump of the variety.
Figure 3:
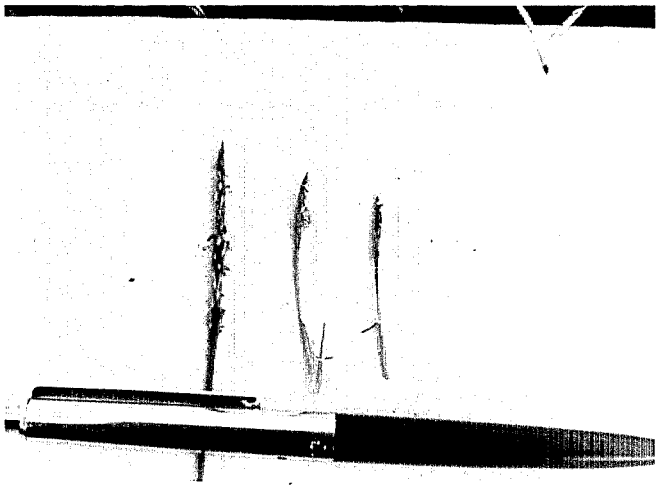
FIG. 3 is a photograph of a tiller of the variety extracted from a closely mowed turf.
Figure 4:
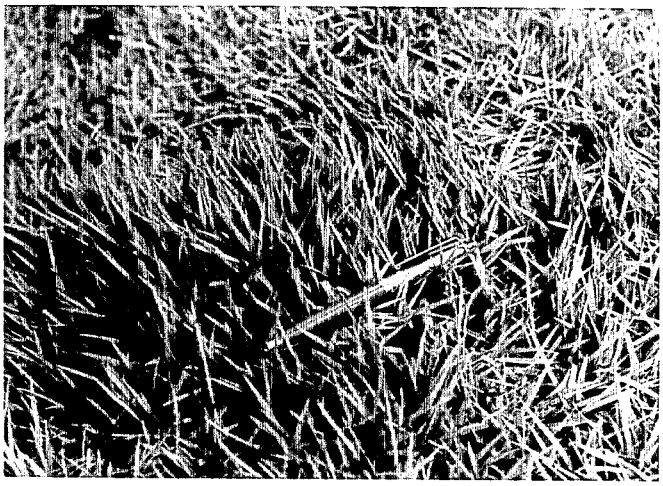
FIG. 4 is a photograph of a clump of the variety (center) compared with 'El Toro' Zoysia grass (left) and with Hawaiian 'Emerald' Zoysia grass (right)
Figure 5:
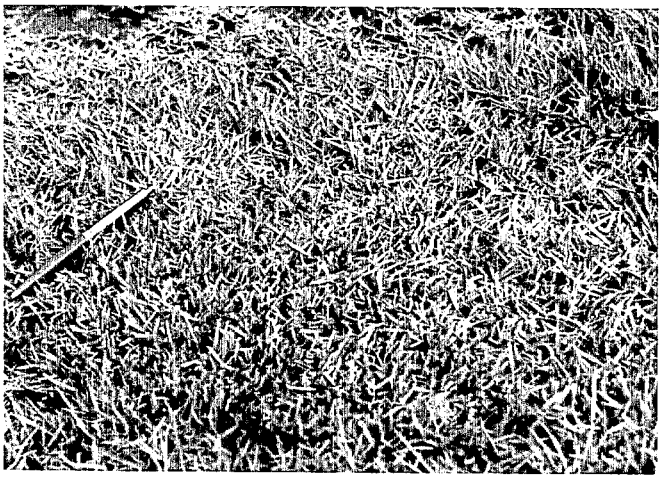
FIG. 5 is a photograph of racemes of the variety bearing inflorescenses in early, middle, and late stages of flowering.
Figure 6:
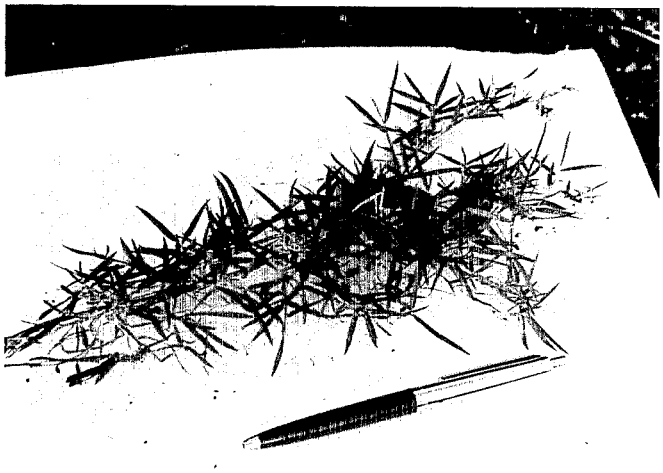
FIG. 6 is a photograph of racemes bearing inflorescences of the variety (center) compared with racemes bearing inflorescenses of 'El Toro' Zoysia grass (left) and Hawaiian 'Emerald' Zoysia grass (right).

Drawings Sheet 1 of 2, replace "Sheet 1 of 2" with --Sheet 2 of 2--;
replace "FIG. 1" with --FIG. 4--;
replace "FIG. 2" with --FIG. 5--; and
replace "FIG. 3" with --FIG. 6--.

Drawings Sheet 2 of 2, replace "Sheet 2 of 2" with --Sheet 1 of 2--;
replace "FIG. 4" with --FIG. 1--;
replace "FIG. 5" with --FIG. 2--; and
replace "FIG. 6" with --FIG. 3--.

Signed and Sealed this

Thirtieth Day of May, 1995

*Attest:*

Bruce Lehman

BRUCE LEHMAN

*Attesting Officer*

*Commissioner of Patents and Trademarks*